United States Patent
Ganesan

(10) Patent No.: US 7,459,907 B2
(45) Date of Patent: Dec. 2, 2008

(54) FLOW MEASUREMENT USING NMR

(75) Inventor: Krishnamurthy Ganesan, Sugar Land, TX (US)

(73) Assignee: Schlumberger Technology Corporation, Sugar Land, TX (US)

( * ) Notice: Subject to any disclaimer, the term of this patent is extended or adjusted under 35 U.S.C. 154(b) by 0 days.

(21) Appl. No.: 11/676,737

(22) Filed: Feb. 20, 2007

(65) Prior Publication Data

US 2008/0174313 A1     Jul. 24, 2008

Related U.S. Application Data

(60) Provisional application No. 60/877,946, filed on Dec. 28, 2006.

(51) Int. Cl.
*G01V 3/00*       (2006.01)

(52) U.S. Cl. ..................................... 324/303

(58) Field of Classification Search .......... 324/300–322
See application file for complete search history.

(56) References Cited

U.S. PATENT DOCUMENTS

| | | | |
|---|---|---|---|
| 4,602,641 A * | 7/1986 | Feinberg | 600/419 |
| 4,714,081 A * | 12/1987 | Dumoulin et al. | 600/419 |
| 4,777,957 A * | 10/1988 | Wehrli et al. | 600/413 |
| 5,025,788 A * | 6/1991 | Dumoulin | 600/413 |
| 5,038,783 A * | 8/1991 | Dumoulin | 600/419 |
| 5,038,784 A * | 8/1991 | Dumoulin | 600/419 |
| 5,428,291 A * | 6/1995 | Thomann et al. | 324/303 |
| 5,684,398 A * | 11/1997 | Takiguchi et al. | 324/306 |
| 6,046,587 A | 4/2000 | King et al. | |
| 6,141,578 A * | 10/2000 | Hardy | 600/410 |
| 6,346,813 B1 | 2/2002 | Kleinberg | |
| 6,380,739 B1 * | 4/2002 | Machida | 324/309 |
| 6,518,757 B1 | 2/2003 | Speier | |
| 6,518,758 B1 | 2/2003 | Speier et al. | |
| 6,528,995 B1 | 3/2003 | Speier et al. | |
| 6,531,869 B1 | 3/2003 | Speier et al. | |
| 6,538,438 B1 | 3/2003 | Speier et al. | |
| 6,549,007 B1 * | 4/2003 | Hills et al. | 324/306 |
| 6,642,715 B2 | 11/2003 | Speier et al. | |
| 6,710,596 B2 | 3/2004 | Speier et al. | |
| 6,841,996 B2 | 1/2005 | Madio et al. | |
| 6,856,132 B2 | 2/2005 | Appel et al. | |
| 6,952,096 B2 | 10/2005 | Freedman | |
| 7,053,611 B2 | 5/2006 | Freedman | |
| 2006/0097722 A1 | 5/2006 | Scheven | |

OTHER PUBLICATIONS

Streeter, Fluid Mechanics, McGraw-Hill Book Co., 5th Edition, p. 244.
Carr et al., The Physical Review, vol. 94, No. 3, pp. 630-638, 1954.

* cited by examiner

*Primary Examiner*—Dixomara Vargas
(74) *Attorney, Agent, or Firm*—Bryan L. White; Reza Taherian; Darla Fonseca

(57) ABSTRACT

A nuclear magnetic resonance (NMR) method is used to determine a velocity distribution or velocity image of a flowing fluid in a downhole environment. The method comprises applying a radio frequency pulse sequence; applying a magnetic field gradient magnetic field and a gradient pulse duration; measuring a NMR signal; determining a phase characteristic of the NMR signal; and determining the velocity distribution or image of the fluid using the determined phase characteristic, the magnetic field gradient pulse parameters, and a time delay between gradient pulses.

18 Claims, 10 Drawing Sheets

FLOW MEASUREMENT USING NMR

CROSS-REFERENCE TO RELATED APPLICATIONS

This application claims priority from and the benefit of U.S. Provisional Patent Application No. 60/877,946, filed Dec. 28, 2006.

BACKGROUND OF INVENTION

1. Field of the Invention

The invention relates generally to flow measurement methods and systems. In particular, embodiments relate to flow measurements using Nuclear Magnetic Resonance (NMR) instruments.

2. Background Art

In industries where a flow of fluid is involved, measurements of flow parameters such as flow velocity and fluid viscosity are often required. Conventional flow measurement technologies include turbine flow meters and positive-displacement flow meters, both of which involve placement of moving parts in the flowing fluid. Moving pails, such as a turbine, disturb the flow pattern of the fluid, thus increasing the complexity of obtaining accurate measurements.

Non-invasive (low measurements such as ultrasonic meters and NMR sensors have certain advantages over conventional flow meters. These advantages include: excellent long-term repeatability, less sensitivity to fluid properties such as viscosity and pressure, higher accuracy, wider range of linearity, and lower cost of maintenance due to the lack of moving parts. Thus, non-invasive flow measurements are particularly well-suited for downhole tools in the oil and gas industry.

U.S. Pat. No. 6,046,587 issued to King et al. discloses methods and apparatus for measuring flow velocity of multiphase fluids flowing in a pipeline. The King et al. patent teaches using the ratio of FID amplitudes of signals acquired with different delay times to infer flow velocity using a single NMR sensor. However, the FID signal is difficult to measure using permanent magnets because static magnetic field variations will result in signals that decay too fast for reliable detection. Moreover, the King et al. methods for determining flow velocity do not account for the fact that there is a distribution of (low velocity in a pipe. In another embodiment, the King et al. apparatus consists of two separated NMR sensors. The flow-velocity and fluid volumes for multiphase fluid flow are computed from FID measurements from the two sensors. However, the computation requires prior knowledge of the fluid $T_1$ distributions.

As known in the field of NMR imaging, to obtain 3-D proton density information in density imaging, a magnetic field gradient needs to be used across a sample to be measured, resulting in a variation of frequency $\omega_a$ over the sample. The magnetic field gradient can also be used to measure flow properties. The magnetic field gradient causes a periodicity in spin density in the sample. In practice, by sending a sequence of RF pulses into the sample, an echo signal can be generated. A typical sequence used in various applications is referred to as a spin-echo sequence, including a 90° pulse, which rotates the net magnetization from the X direction down to the Y-Z plane, followed by a 180° pulse, which rotates the magnetization by 180° about the Y axis. The 180° pulse re-phases the magnetization thus producing a signal, i.e., the spin-echo signal. Intuitively, an RF pulse can cause spin excitations in a fluid, and if the fluid is flowing, a group of nuclei in excited state is carried by the flow. An echo signal in a time axis carries information on the flow properties such as the flow velocity.

In addition to flow properties, other reservoir fluid properties can be measured using an NMR module in a downhole tool, such as the fluid sampling tool disclosed in U.S. Pat. No. 6,346,813 B1 issued to Kleinberg. An example of formation fluid tester tool is the Modular Formation Dynamics Testing tool marketed under the trade name of MDT™ by Schlumberger Technology Corp. (Houston, Tex.).

FIG. 1 shows an exemplary formation fluid testing tool body 10 (e.g., an MDT™ tool) that houses the following modules: an electric power module 11; a hydraulic power module 12; a probe module 13, which may be deployed to make a hydraulic seal with the formation; an optical fluid analyzer module 14; an NMR module 15, a multi-sample module 16, and a pumpout module 17. In addition, the tool body 10 may enclose a processor and a memory for downhole data collection and processing. The tool body 10 is designed to work in harsh downhole environments.

The NMR module 15 may include an NMR sensor, which includes a magnet that can produce a substantially homogeneous static magnetic field over the volume of the fluid sample. In addition, the NMR sensor includes at least one coil that can produce pulsed field gradients (PFG) of defined amplitudes and time durations across the sample volume. A homogeneous static magnetic field in combination with a PFG can provide measurements with better signal-to-noise ratios because a larger sample volume is resonated, as compared to a static magnetic field having a static field gradient, which can only excite a small portion of the sample (a "sample slice") to resonate. The NMR sensor also includes a coil (an RF antenna) for producing RF pulses. The magnetic moment of the RF antenna is substantially perpendicular to the magnetic moment of the static magnetic field.

U.S. Pat. No. 6,952,096, issued to Freedman on Oct. 4, 2005, and also assigned to the assignee of the present invention, discloses an NMR sensor and a pulse sequence used to measure a flow velocity. The NMR sensor includes some basic elements such as a magnet to generate a substantially homogeneous "base" field and RF antenna to excite a portion of the flow.

FIG. 2A shows an illustration of an NMR sensor 20 disclosed by Freedman in U.S. Pat. No. 6,952,096, for determining flow velocity and other properties of a fluid flowing in a flowline (or flow pipe) 22. A magnet 24 and an RF antenna 26 are included in the NMR sensor 20.

The flowline 22 includes a pre-polarization section 28 that is upstream of an investigation section 29. The magnet 24 is disposed around both the pre-polarization section 28 and the investigation section 29. The magnet 24 may be a permanent magnet or an electromagnet. The flowline 22 is typically made of a non-conductive and non-magnetic material, such as a composite or polymer material. However, if the flowline 22 is made of a conductive or magnetic material (e.g., steel), then the antenna 26 should be located inside the flowline.

For the NMR sensor 20 shown in FIG. 2A, the antenna (solenoid coil) 26 functions as both a transmitter and a receiver. When functioning as a transmitter, the RF antenna emits RF electromagnetic pulses along the direction of the RF antenna. The RF antenna 26 substantially covers the investigation section 29 of the flowline 22.

The NMR measurements include a suite of variable wait time (W) measurements. Prior to each wait time (W), the magnetization is first spoiled by pulses designed to "kill" the magnetization so that $M_X=M_Y=M_Z=0$. Following the spoiling pulse and the wait time, a 90° pulse followed by a 180° pulse (e.g. a spin-echo pulse) is applied to the transmitter to generate a spin echo. The measurements are repeated for a number of different wait times. Multiple 180° pulses may be applied to produce multiple spin-echo signals.

The amplitudes of the detected spin-echo signals for the different wait times depend on flow velocity, wait time, receiver and transmitter antenna lengths, magnet pre-polarization length, and the $T_1$ distribution of the fluid. All of these parameters, except the flow velocity and the $T_1$ distribution of the fluid, are either fixed by the sensor design or by the pulse sequence. If sufficient sets of measurements are available, these parameters may be derived by fitting the measured signals to a proper model that simulates the NMR response of the flowing fluid. That is, the data may be interpreted by forward modeling.

A theoretical forward model can be used to simulate the echo signals for any combination of the aforementioned pulse sequence, sensor parameters, flow velocity, and $T_1$ distribution. The forward model may be used iteratively in an inversion to determine the apparent flow velocity and $T_1$ distribution. Alternatively, if the flow velocity is known from other measurements, the forward model can be lit by inversion to determine the $T_1$ distribution.

FIG. 2B shows that the velocity- and position-dependent polarization profile f(v,z) over the length $l_a$ of the receiver coil (shown as 26 in FIG. 2A) is made of two parts. The first part comes from fresh spins that are "pre-polarized" as they travel in the static magnetic field into the receiver during the wait time W. The second part comes from spins that were in the receiver coil and are "re-polarized" during the wait time. The pre-polarization length $l_p$ shown in FIGS. 2A and 2B corresponds to the length of the pre-polarization region 28.

The polarization function is given by $$f(v, z) = 1 - \exp\left(-\frac{T(z, v)}{T_1}\right), \quad (1)$$

where T(z, v) is the polarization time for a spin with position z and velocity v, and $T_1$ is the longitudinal relaxation time of the spins. The polarization time, T(z,v), is defined as:

$$T(z, v) = \frac{l_p + z}{v} \text{ for } 0 \leq z \leq v \cdot W \quad (2a)$$

and, $$T(z, v) = W \text{ for } v \cdot W < z \leq l_a. \quad (2b)$$

It is clear from the above equations that the polarization function, $f(v,z)$, also depends on $l_p$, W, and $T_1$. Those dependencies are implicit in Eq. 1. The polarization time, T(z, v), is used to simplify the notation, but depends on $l_p$ and W as z ranges over the defined intervals. These equations can be more easily understood following a discussion of the variable wait time (VWT) pulse sequence shown in FIGS. 3A and 3B.

FIG. 3A shows a suite of VWT pulses consisting of N measurements. N is typically on the order of 10. At the conclusion of each measurement in the suite, one or more spoiling pulses (collectively denoted by the pulse S) are applied to destroy any remnant magnetization before starting the wait lime for the next measurement. The duration and frequencies of the spoiling pulses are instrument dependent and can be determined empirically.

As shown schematically by the $k^{th}$ measurement in FIG. 3B, following each wait time a 90° excitation pulse is applied to rotate the longitudinal magnetization into the transverse plane. The signal from the transverse magnetization rapidly de-phases due to inhomogeneity (or other factors) in the static magnetic field, but is refocused by the 180° pulse to produce a spin-echo signal. After the spin-echo signal is acquired a spoiling pulse is applied to remove the magnetization of the spins within the receiver coil. Other VWT sequences similar to the one shown in FIGS. 3A and 3B can also be used to observe FID signals instead of a spin-echo signal. Both the inversion-recovery and the saturation-recovery pulse sequences are generally referred to as "$T_1$-relaxation investigation pulse sequences."

The pulse sequence used to acquire the NMR signals (FID or spin-echo signals) are generally referred to as an "acquisition pulse sequence." An acquisition pulse sequence may include a single 90° pulse, a spin-echo pulse (i.e., a 90° pulse followed by a 180° pulse), and the variants of the spin-echo pulse such as the Carr-Purcell-Meiboom-Gill (CPMG) sequence, i.e., multiple 180°, refocusing pulses following a single 90° excitation pulse.

The "variable wait time pulse sequence" as shown in FIGS. 3A and 3B comprises a spoiling pulse, a wait time, and an acquisition pulse sequence. The spin-echo pulse sequence and its variants (e.g., CPMG) are generally referred to as a "spin-echo pulse sequence." That is, a "spin-echo pulse sequence" not only includes a single 90° pulse and a single 180° pulse, but also may include multiple 180° pulses after the 90° pulse.

During each wail time, fresh or pre-polarized spins move into the antenna region. Equation (2a) shows that in the region. $0 \leq z \leq vW$, fresh spins have entered the antenna during the wait time. The length of this region depends on v and W. The polarization time for these fresh spins is independent of W. Instead, it depends on the duration that the spins have been exposed to the static magnetic field since they entered the field of the permanent magnet. This is because this portion of the fluid is outside the transmitter/receiver antenna (shown as 26 in FIG. 2A) when the spoiling pulse is applied and the magnetizations of the spins in this portion of the fluid are not "killed" by the spoiling pulse. On the other hand, as can be seen from Eq. (2b), the re-polarization of the spins in the adjoining region of length, i.e., from v·W to $l_a$, is controlled by W because these spins were in the transmitter/receiver region when the spoiling pulse was applied. The magnetizations of these spins were removed by the spoiling pulse, and any polarization detected by the receiver is due to re-polarization during W. If W is long or v is fast enough such that v·W exceeds the antenna length, then only fresh spins (those that enter the receiver antenna after the spoiling pulse) are measured and the polarization function is independent of W.

U.S. Pat. No. 6,841,996, issued to Madio et al. on Jan. 11, 2005, discloses methods for measuring the velocity of fluids flowing through a flowline of a fluid sampling tool. The method exploits the fact that there is a spin echo signal phase shift between different wait time measurements in a VWT pulse sequence. The measured phase shifts are proportional to both the flow velocity and a static magnetic field gradient. In addition, Madio et al. show a linear relationship between the phase difference of odd and even echoes and the product of the flow velocity and the static magnetic field gradient, up to a flow velocity of 6 cm/sec. At higher flow velocities, the phase difference is no longer an adequate velocity indicator.

Forward models can be used to predict the NMR sensor signals, which depends on the flow velocity, the distribution of $T_1$, the wait time, and geometrical parameters such as the antenna length, the magnet pre-polarization length, and the radius of the flowline. For a given wait lime and a sensor design, the only variables in the forward model are the flow velocity and the $T_1$ distribution of the fluid. The flow velocity and $T_1$ distribution are determined by inversion. The forward model is derived in the following paragraphs.

To accurately model die NMR signals from flowing fluids, the fact that the velocity profile of a laminar flow for a viscous fluid flowing in a pipe is parabolic should be taken into account. See, e.g., Streeter, "*Fluid Mechanics.*" McGraw-Hill Book Co., $5^{th}$ Edition. p. 244. In a laminar flow, the maximum flow velocity, $v_m$, occurs at the axis of the pipe, while the velocity is zero at the wall of the pipe. The laminar flow regime in circular pipes is characterized by the values of Reynolds number, $R \leq 2000\text{--}3000$, where the exact upper limit for laminar flow depends on the surface roughness of the pipe. The Reynolds number is defined by $$R = \frac{2r_o v \rho}{\eta}, \quad (3)$$

where $r_o$ is the radius of the flowline, v is the average flow velocity, $\rho$ is the fluid mass density, and $\eta$ is the viscosity of the fluid. In contrast to a laminar flow, turbulent flow has a chaotic component and is much more difficult to model. One feature of turbulent flow is a flattening of the velocity parabolic profile. FIG. 4 shows the velocity profiles for laminar flow and non-laminar flow in a circular pipe.

For a laminar flow the velocity profile is parabolic and can be written in the form, $$v(r) = -\frac{(r^2 - r_0^2)}{r_0^2} v_m \quad (4a)$$

where $v_m$ is the maximum flow velocity on the axis of the flowline (i.e., at r=0) as shown in FIG. 4. It follows from Eq. (4a) that the average flow velocity with a laminar flow is $v_m/2$. While Eq. (4a) describes a commonly used model for laminar flow, an alternative laminar flow model may be described as follows;

$$v(r) = v_m \left(1 - \frac{r}{r_0}\right)^{1/n} \quad (4b)$$

where n is typically between 5 and 10.

The velocity profile for the non-laminar flow depicted in FIG. 4 can be described by the following equations:

$$v(r) = v_m \text{ for } 0 \leq r \leq a, \quad (5a)$$

and, $$v(r) = -\frac{\{(r-a)^2 - (r_0-a)^2\} v_m}{(r_0-a)^2} \text{ for } a \leq r \leq r_0. \quad (5b)$$

The flow models described above can be used to derive flow profiles in
conjunction with NMR signals.

FIG. 5 illustrates a spin-echo pulse sequence that can be used to measure a flow velocity, as disclosed by Carr and Purcell (the Physical Review, v. 94, no. 3, pp. 630-638, 1954).

The ratio of even to odd spin echo amplitude, e.g., the ratio between the amplitudes of the even spin-echo signal 52 and the odd spin-echo signal 51' is proportional to the flow velocity. Thus, by measuring the amplitudes of the spin-echo signals, the flow velocity can be derived.

U.S. Pat. Nos. 6,518,757, 6,518,758, 6,528,995, 6,531,869, 6,538,438, 6,710,596, 6,642,715, issued to Speier et al., and also assigned to the assignee of the present invention, disclose obtaining flow velocity information in the formation from the amplitude of the spin echo.

U.S. Pat. No. 6,856,132 issued to Appel et al., discloses obtaining flow velocity information in the formation in the presence of a static magnetic field gradient.

SUMMARY OF INVENTION

A nuclear magnetic resonance (NMR) tool and method are used to determine a velocity distribution or velocity image of a flowing fluid in a downhole environment. The method comprises applying a radio frequency pulse sequence; applying a magnetic field gradient pulse sequence, wherein each magnetic field gradient pulse has parameters including a gradient magnetic field and a gradient pulse duration; measuring a NMR signal; determining a phase characteristic of the NMR signal: and determining the velocity distribution or image of the fluid using the determined phase characteristic, the magnetic field gradient pulse parameters, and a time delay between gradient pulses.

Embodiments disclosed herein relate to a downhole system to determine a flow property of a formation fluid flowing in a flowline, comprising a formation fluid testing tool and a nuclear magnetic resonance tool.

Other embodiments disclosed herein related to a method to determine the magnitude of a gradient magnetic field using a nuclear magnetic resonance tool disposed in a wellbore, comprising applying a radio frequency pulse sequence; applying a magnetic field gradient pulse sequence, wherein each magnetic field gradient pulse has parameters including a gradient magnetic field and a gradient pulse duration; measuring a NMR signal in the presence of a gradient pulse; determining a frequency spread from the NMR signal; and determining the magnitude of the gradient magnetic field using the frequency spread.

Other aspects and advantages of the invention will become apparent from the following description and the attached claims.

DETAILED DESCRIPTION

Specific embodiments of the invention will now be described with reference to the figures. Like elements in the various Figures will be referenced with like numbers for consistency.

Embodiments of the invention relate to a method and apparatus for measuring flow properties, particularly a flow velocity, based on measuring a phase of an NMR signal. To obtain an NMR signal with a measurable phase, a magnetic field gradient pulse is used to shift the phase of the NMR signal.

U.S. Pat. No. 7,053,611, issued to Freedman on May 30, 2006, and assigned to the assignee of the present invention, has disclosed an NMR sensor that includes means for generating a pulsed magnetic field gradient (PFG). This NMR sensor exploits NMR signal amplitude information, but not phase information. The structure of the NMR sensor and pulse sequences disclosed by Freedman in the 611 patent is described in the following paragraphs with reference to FIG. 6 to facilitate the understanding of a basic NMR sensor structure, and particularly the means for generating a pulsed magnetic field gradient.

Figure 6:
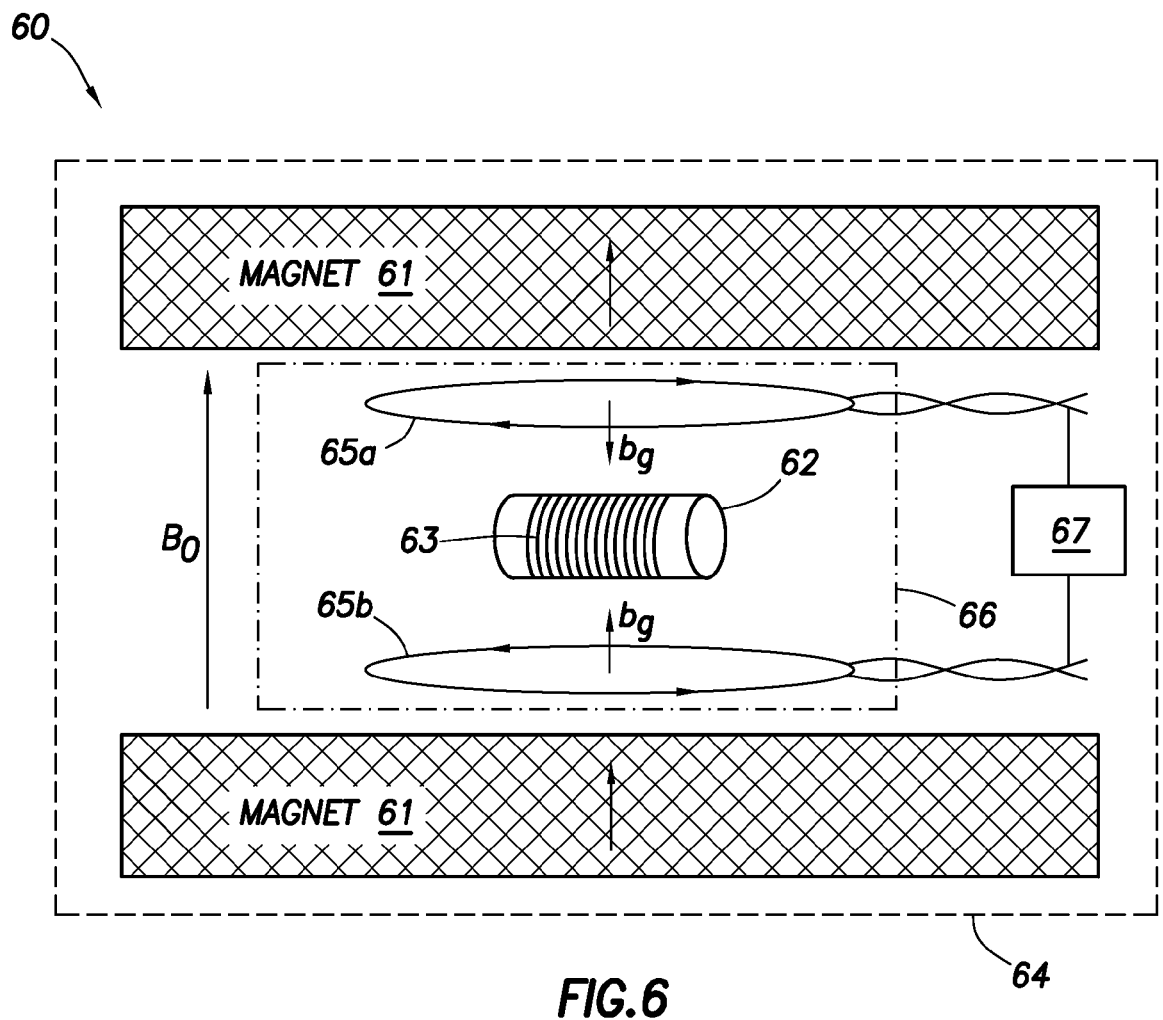
FIG. 6 shows an NMR sensor having a magnetic field gradient orthogonal to a flowline direction in accordance with an embodiment of the invention.

As shown in FIG. 6, the NMR sensor 60 includes a magnet 61 designed to produce a substantially homogeneous magnetic field ($B_0$) in a sample volume 62. The magnet 61 may be a permanent magnet made of Samarium Cobalt or any other suitable material. Alternatively, the magnet 61 may be an electromagnet. The magnet 61, which may comprise a single piece or several pieces that surround the sample volume 62, may further include permeable pole pieces attached to its surfaces for shaping the magnetic field and for reducing the magnetic field gradient in the sample region so that $B_0$ is substantially homogeneous over the sample volume 62.

The sample volume 62 is configured to be connected to a formation fluid flowline so that the sensor 60 can be used to measure or monitor the properties of the fluid flowing through the flowline. An RF antenna (coil) 63 surrounds the sample volume 62. The RF antenna 63 is designed to radiate an oscillating RF magnetic field ($B_1$), i.e., an RF pulse, having a magnetic moment substantially perpendicular (orthogonal) to that of the static magnetic field $B_0$ produced by the magnet 61. The RF antenna 63 may comprise a solenoid coil, a saddle coil, or any other suitable coil. The same RF antenna 63 may function as a transmitter to transmit the oscillating magnetic field, and as a receiver to receive the signals. Alternatively, separate transmitter and receiving antennas may be used.

The NMR sensor 60 shown in FIG. 6 also includes two gradient coils 65a and 65b that are configured to produce a magnetic field gradient across the volume of the sample 62. As is known in the art, the gradient coils 65a and 65b produce a linear gradient along the direction of the flowline. The gradient coils 65a and 65b are connected to a control unit 67 that can energize the gradient coils 65a and 65b at a selected amplitude for a predetermined time duration. While two gradient coils 65a and 65b are shown, one of ordinary skill in the art would appreciate that one or more gradient coils may be used. During the time duration of a gradient pulse, opposing magnetic fields $b_g$ may be created to induce a magnetic field gradient g over the sample volume. The magnitude of the magnetic field gradient g is usually measured in units of Gauss/cm. The sensor 60 may be protected and supported by a housing 64. The housing 64 may be made of a magnetic steel with high magnetic permeability for confining the magnetic field $B_0$ and for providing strength to the assembly.

A shield 66 may be included for separating the RF antenna 63 and the magnet 61. The shield may be made of a material (e.g., copper) that can prevent the oscillating RF magnetic field produced by the RF antenna 63 from interacting with the magnet 61 so that magneto-acoustic ringing in the magnet can be minimized.

The NMR sensor 60 can be used for measurements related to the diffusion and relaxation properties of fluid samples. Because these properties are generally different for oil and water, these measurements can provide means for determining the relative proportion of water and oil in a fluid sample. In addition, these measurements can provide information on oil properties such as composition, viscosity, and gas/oil ratio (amount of dissolved gas contained in the oil). Similarly, for a fluid sample, which may comprises (1) gas and water, (2) gas, oil, and water, (3) oil and gas, or (4) oil and water, the measurements can provide a means for determining the relative proportions of the different components. In addition, these measurements can provide information on the hydrocarbon properties that are important for determining the economic value of the reservoir that are essential for making well completion decisions.

U.S. Patent Application Pub. No. 20060097722 by Scheven and also assigned to the assignee of the present invention, discloses obtaining velocity information in the formation using stimulated echo sequences in the presence of a static magnetic field gradient.

Figure 7:
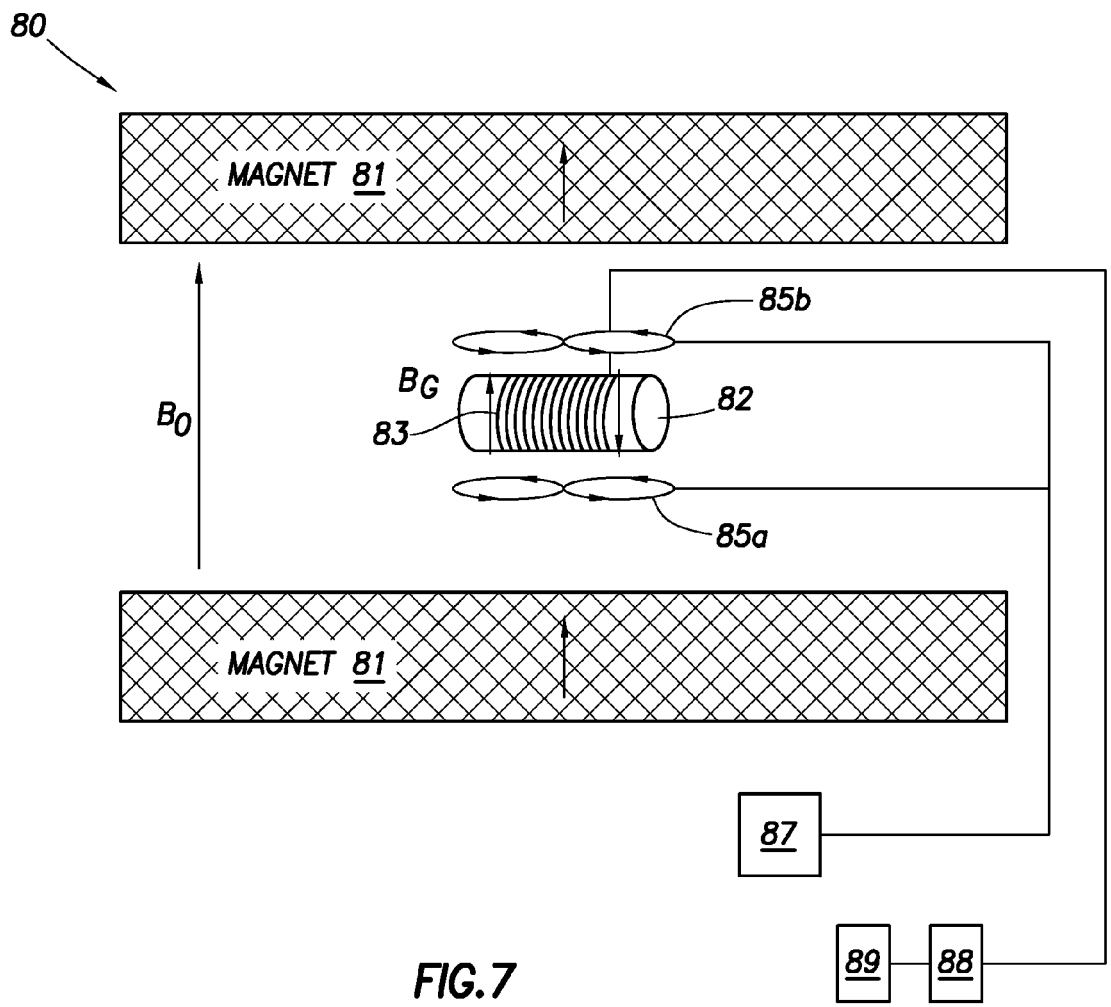
FIG. 7 shows an NMR sensor having a magnetic field gradient along a flowline direction in accordance with an embodiment of the invention.

Embodiments of the present invention exploit information carried by the phases of spin-echo signals. A magnetic field gradient pulse is used to shift die phase of the spin-echo signals. An NMR sensor 80 is shown in FIG. 7. Similar to the NMR sensor 60 of FIG. 6, the sensor 80 also includes a magnet 81 designed to produce a substantially homogeneous magnetic field ($B_0$) in a sample volume 82.

An RF antenna (coil) 83 surrounds the sample volume 82. The RF antenna 83 is designed to radiate an oscillating RF magnetic field ($B_1$), i.e.,. an RF pulse, having a magnetic moment substantially perpendicular (orthogonal) to that of the static magnetic field $B_0$ produced by the magnet 81. The RF antenna 83 may comprise a solenoid coil, a saddle coil, or any other suitable coil. The same RF antenna 83 may function as a transmitter to transmit the oscillating magnetic field arid as a receiver to receive the signals. Alternatively, separate transmitter and receiving antennas may be used.

The NMR sensor 80 shown in FIG. 7 also includes two gradient coils 85a and 85b that are configured to produce a magnetic field gradient across the sample volume 82 substantially along the flowline. The gradient coils 85a and 85b are connected to a control unit 87 that can energize the gradient coils 85a and 85b at a selected amplitude for a predetermined time duration. While two gradient coils 85a and 85b are shown in the exemplary configuration, one of ordinary skill in the art would appreciate that using just one gradient coil may be sufficient. Alternatively, more than two gradient coils may be used. In addition, the orientation of the gradient coils may be different from that shown in FIG. 7. So long as the gradient coil(s) provides a component of magnetic field gradient along the flowline, i.e., in line with or opposite to the flow direction, a spin-echo signal would have a shifted phase that can be exploited for measuring a flow velocity as discussed below.

Figure 1:
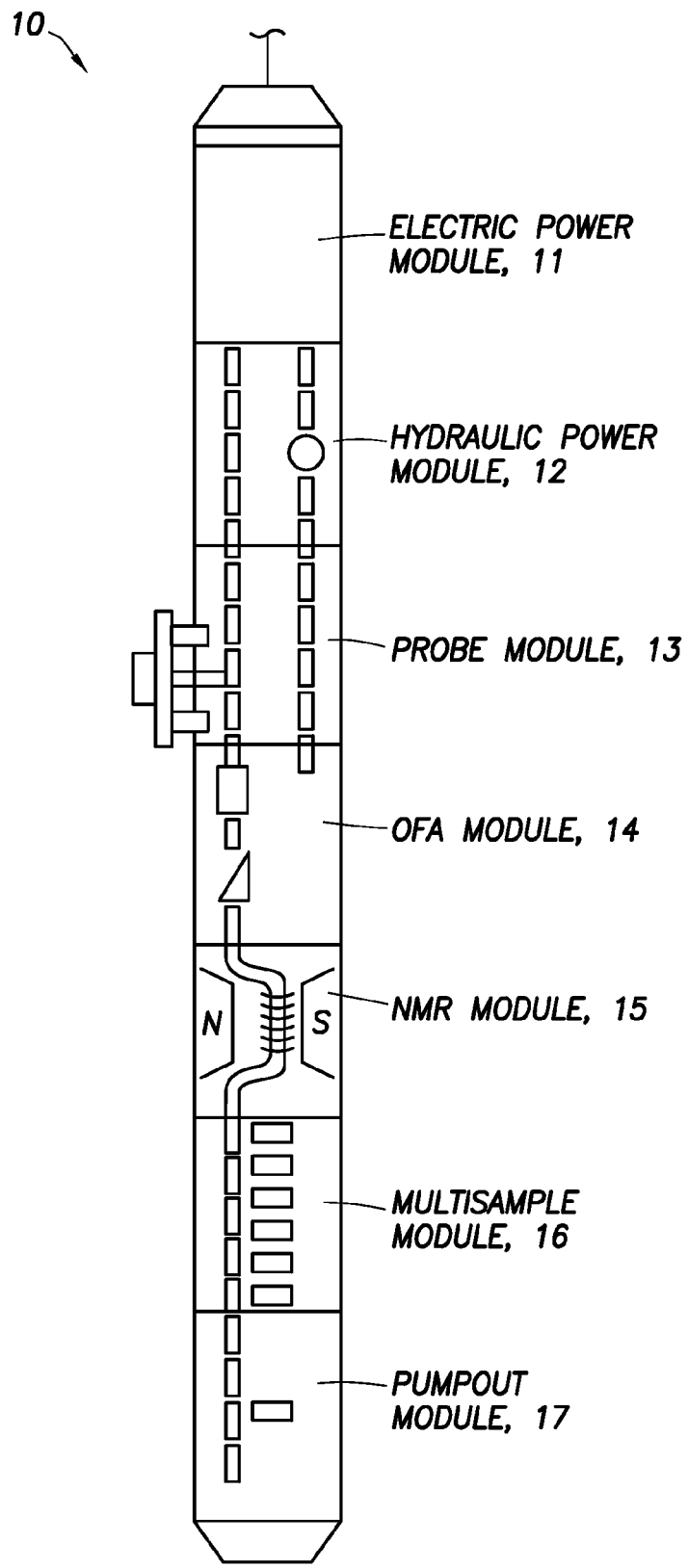
FIG. 1 shows a prior art formation fluid testing tool including an NMR module.
Figure 2A:
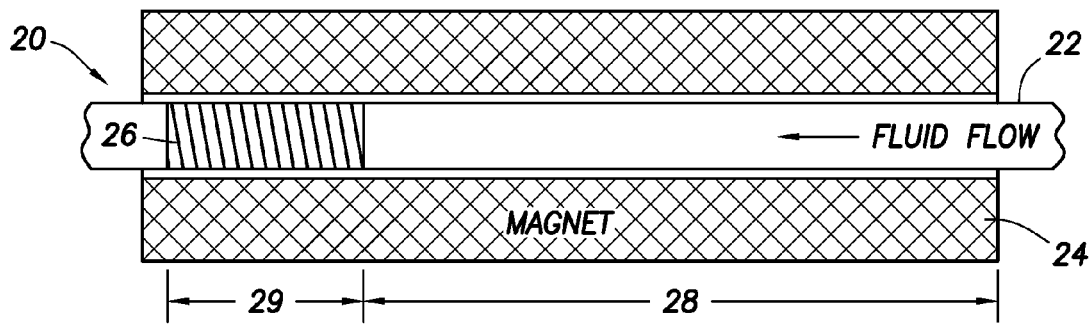
FIG. 2A shows a schematic of a prior art NMR sensor.
Figure 2B:
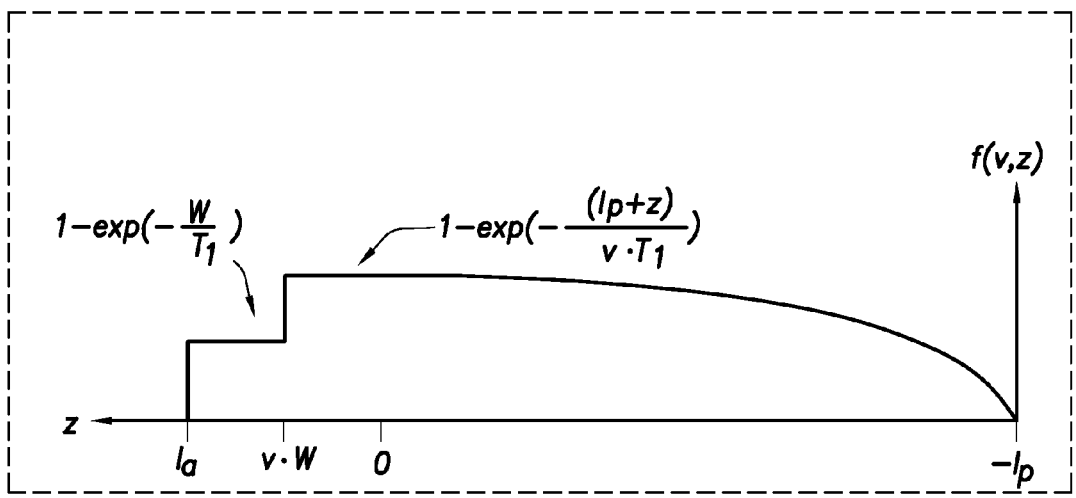
FIG. 2B shows a spin-polarization profile along a flowline in the NMR sensor of FIG. 2A.
Figure 3A:
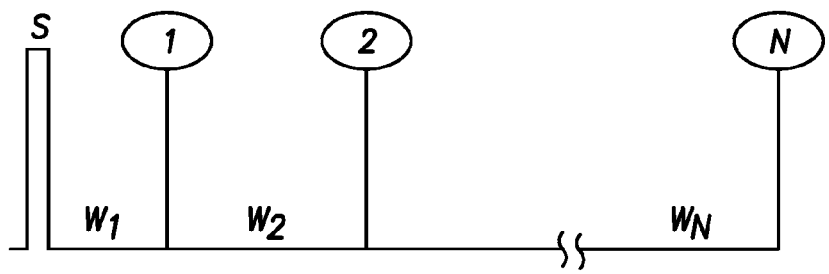
FIG. 3A illustrates a pulse sequence for acquiring VWT NMR measurements.
Figure 3B:
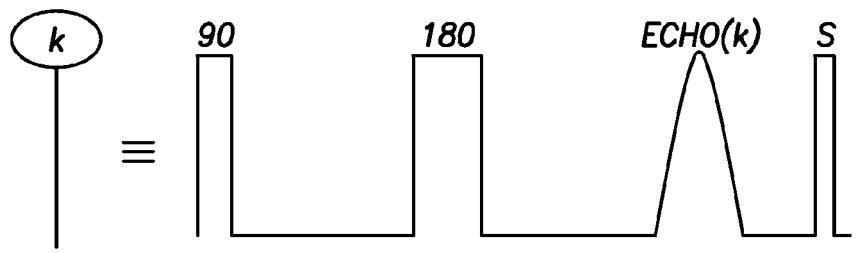
FIG. 3B illustrates a pulse sequence including a spoiling pulse.

The NMR sensor 80 may further include a phase measuring unit 88 and a calculation unit 89. The phase measuring unit 88 is used to measure the phases of the signals received by the RF antenna 83. The calculation unit 89 then uses the measured signal phases 10 derive a flow velocity. As known to those of ordinary skill in the art, the phase measuring unit 88 and the calculation unit 89 may be embodied within the downhole tool 10 shown in FIG. 1 Alternatively, the data can be sent to the surface via an uphole data link and analyzed at the surface.

During a gradient pulse, magnetic, fields $B_G$ are created to induce a magnetic field gradient G, usually measured in units of Gauss/cm, over the sample volume 82. The sensor 80 may be protected and supported by a housing (not shown) and may include a shield (not shown) similar to those in FIG. 6.

Figure 8:
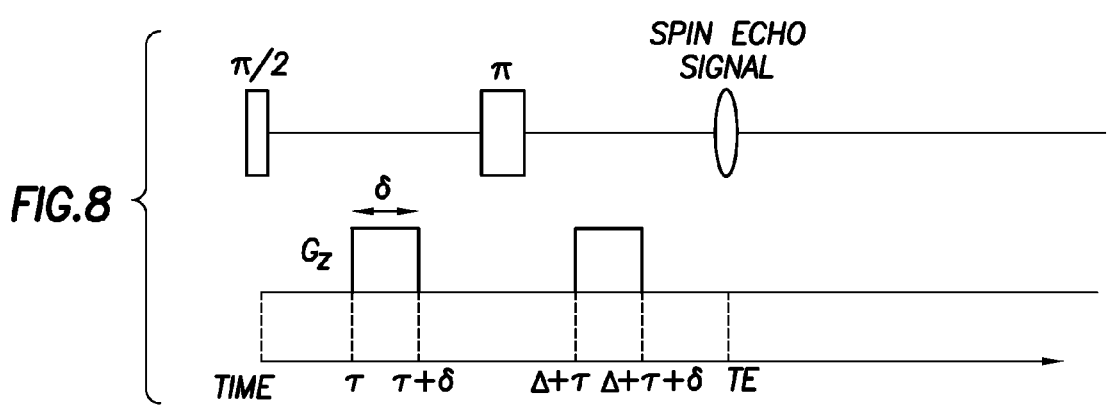
FIG. 8 shows a pulse sequence for generating a phase shift for flowing spins in a spin-echo signal in accordance with an embodiment of the invention.

A PFG spin-echo sequence in accordance with an embodiment of the invention is shown in FIG. 8. A first magnetic field gradient pulse $G_Z$, which is along the Z-axis, i.e., the flowline direction, is applied between the 90° RF tipping pulse and the 180° RF re-focusing pulse. In the embodiment shown, a second magnetic field gradient pulse of the same amplitude and the same time duration is applied alter the 180° RF pulse, but before the spin-echo is formed. Those of ordinary skill in the art will appreciate that two field gradient pulses with different amplitudes and time durations may be used. The field gradient pulse $G_Z$ causes a measurable phase shift in the spin-echo signal.

The phase accumulation of spins can be calculated using $$\Phi(i) \propto \gamma \int_{t1}^{t2} G(t) \cdot r(t) dt, \quad (6)$$

where $\gamma$ is a gyromagnetic ratio, which is usually that of protons, r(t) defines the position of a spin in space as a function of time, and G(t) is the magnetic field gradient, which is a vector and also a function of time. It is noted that G(t) can result from a static magnetic field, or from a pulsed magnetic field.

Assuming the flow direction is along the Z axis, the phase accumulation of spins is $$\Phi(t) \propto \gamma \int_{t1}^{t2} G_Z(t) z(t) dt. \quad (7)$$

The position of spin as a function of time can be expressed as $$Z = Z_0 + v_Z t + 0.5 a t^2, \quad (8)$$

where $z_0$, is the initial position of the spin, $v_z$ is the flow velocity, and $\alpha$ is the acceleration. For a constant-velocity flow, i.e., $\alpha = 0$, we have $$\Phi(t) \propto \gamma \int_{t1}^{t2} G_Z(t)(Z_0 + v_Z t) dt. \quad (9)$$

For the sequence shown in FIG. 8, $G_Z(t)$ is a non-zero constant when time is between $\tau$ and $\tau+\delta$ or between $\Delta+\tau$ and $\Delta+\tau+\delta$, and $G_Z(t)$ is zero otherwise. Thus, the phase shift due to the first applied gradient pulse is given by $$\phi(t) \propto \gamma \int_{\tau}^{\tau+\delta} G_z(z_0 + v_z t) dt = +\gamma G_z z_0 \delta + \gamma G_z v_z [(\tau+\delta)^2 - \tau^2]/2. \quad (10a)$$

The phase shift due to the second applied gradient pulse is given by $$\phi(t) \propto -\gamma \int_{\Delta+\tau}^{\Delta+\tau+\delta} G_z(z_0 + v_z t) dt = \\ -\gamma G_z z_0 \delta - \gamma G_z v_z [(\Delta+\tau+\delta)^2 - (\Delta+\tau)^2]/2. \quad (10b)$$

The phase shift at the echo time (t=TE) is given by combining Eq. (10a) and Eq. (10b), $$\Phi(TE) = -\gamma G_Z v_Z \Delta \delta, \quad (11)$$

where $\delta$ is the time duration of the gradient pulse, $\Delta$ is the time delay between the two gradient pulses, $G_Z$ is the gradient amplitude along the flow direction, and $v_Z$ is the flow velocity.

Figure 9:
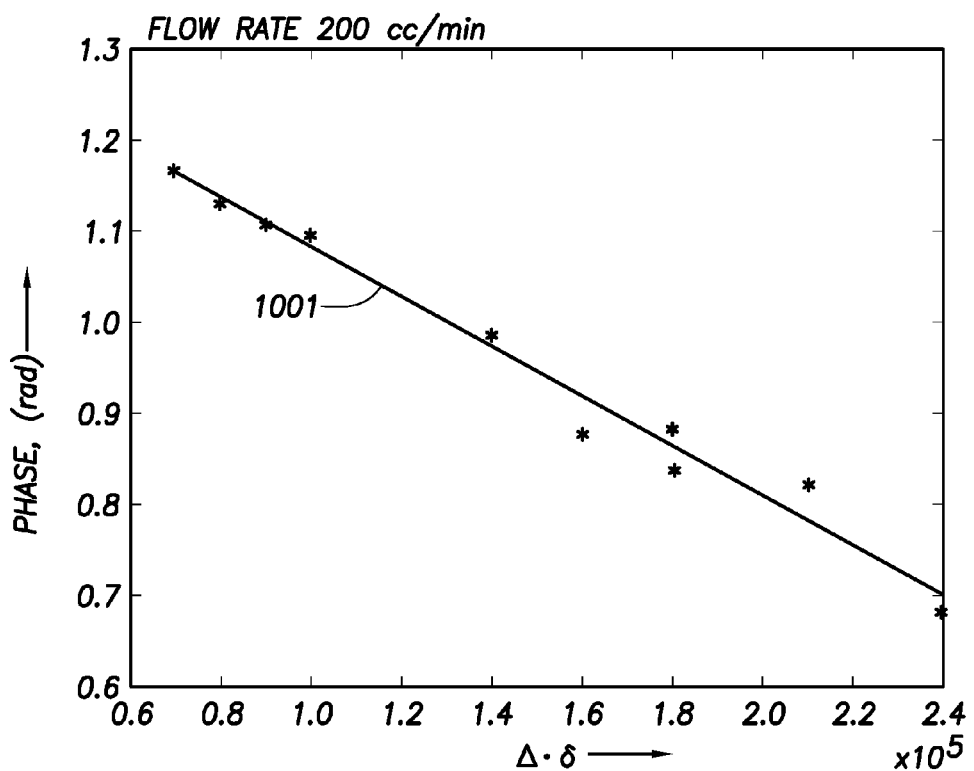
FIG. 9 shows a linear fit to phase data used to derive a velocity for a flow rate of about 200 cc/min.

The above method has been verified in experiments with water flowing in a flowline. The measured phases of spin-echo signals as a function of $\Delta\delta$ for constant $G_Z$ and $v_Z$ are shown in FIG. 9. A linear relation determined using a least-square method is also shown. The effective flow velocity can be calculated from the slope of the line 1001 if the gradient amplitude $G_Z$ is known. Those of ordinary skill in the art would recognize that other curve fitting methods may be used. Further, the relation may not be linear. Other relations may also be exploited. Similarly, the measured phases of spin-echo signals as a function of $G_Z$ for constant $\Delta\delta$ and $v_Z$ lead to a linear relation. Thus, Eq. (11) can be exploited to obtain flow velocity by varying any one of, or any combination of, $\Delta$, $\delta$, and $G_Z$.

To test the accuracy of the method, the flow velocity derived using the line 1001 and Eq. (11) is compared with an effective flow velocity obtained from a different method. For example, the effective flow velocity can be calculated from the known flow rate (F) and the area of cross section (A) of the flowline using the equation $$v_{effective} = \frac{F}{A}. \quad (12)$$

For a particular experiment, the effective flow velocity calculated from Eq. (12) is 14.9 cm/sec for a flow rate of 200 cc/min. This compares to the value of 12.8 cm/sec obtained using the method of the invention.

Figure 10:
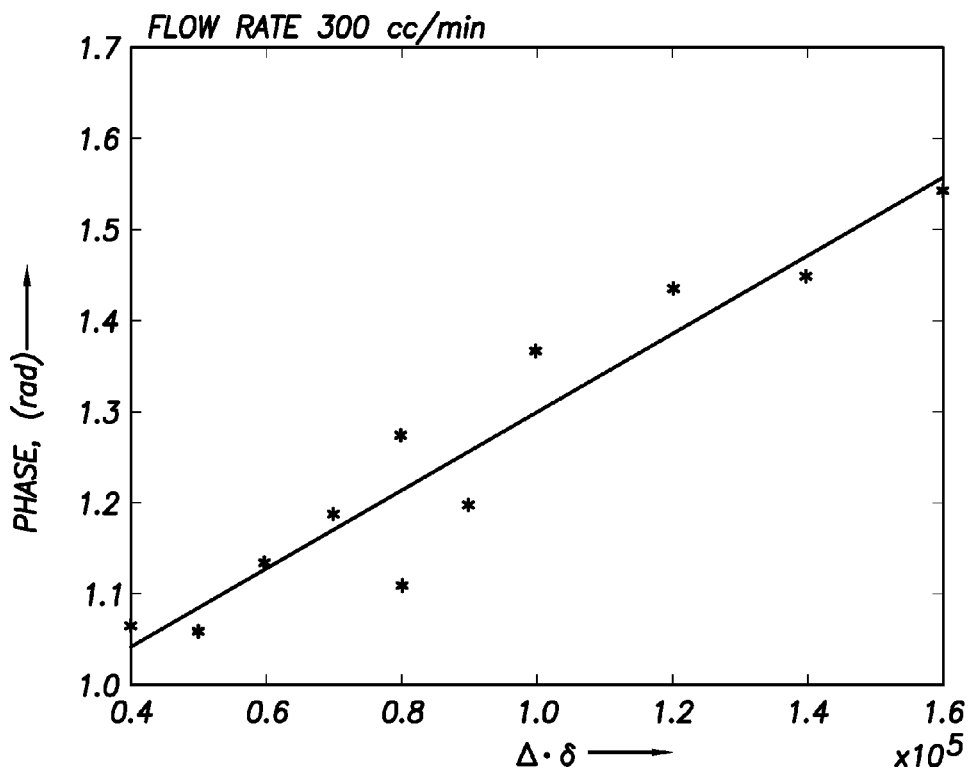
FIG. 10 shows a linear fit to phase data used to derive a velocity for a flow rate of about 300 cc/min.

Data points for the same experiment using a flow rate of 300 cc/min are plotted in FIG. 10. The flow velocity derived using the method of the present invention is 20 cm/sec, and the calculated effective flow velocity using Eq. (12) is 22.4 cm/sec.

Figure 11:
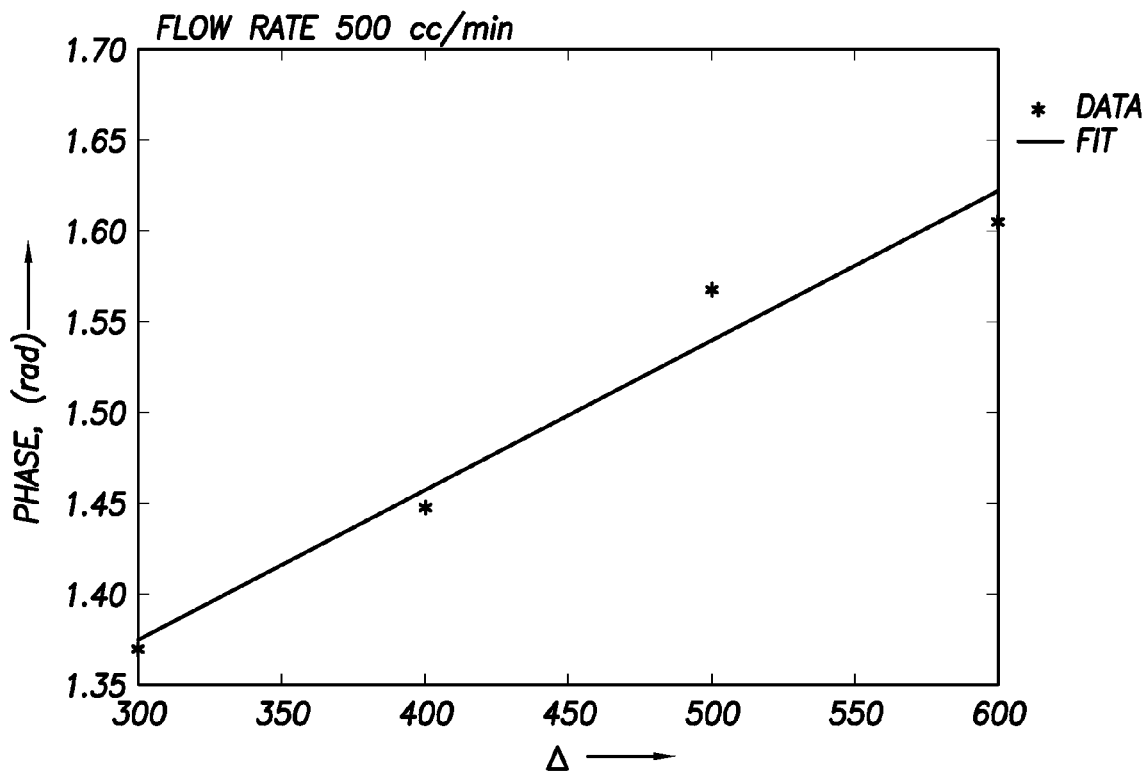
FIG. 11 shows a linear fit to phase data used to derive a velocity for a flow rate of about 500 cc/min.

For a flow with a flow rate of 500 cc/min, a similar plot and curve fitting are illustrated in FIG. 11. Note the measured phases are plotted against $\Delta$ only, rather than $\Delta\delta$ as in FIGS. 9 and 10. Using the slope of the line in FIG. 11 and given values for $\delta$ and $v_Z$, the flow velocity is determined to be 38.7 cm/sec, and the calculated effective flow velocity using Eq. (12) is 37.3 cm/sec.

Note the slope of the fitted line 1001 in FIG. 9 is negative while the slopes of the lines in FIGS. 10 and 11 are positive. This is because the flow direction for the data in FIG. 9 is opposite to the flow direction for the data in FIGS. 10 and 11. In this description, the term "direction of the flowline" includes both flow directions in the flowline. Note that changing the sign of $G_Z$ will also change the sign of the slope.

Also note that when using Eq. (11), the values of $\Delta$, $\delta$, and $G_Z$ are controlled such that the measured phase is preferably less than 360°. Otherwise, phase wrapping may occur. In the data range shown in FIGS. 9-11, a linear relation is maintained, indicating no phase wrapping.

The amplitude of the gradient $G_Z$ may be predetermined in designing the configuration of the NMR sensor. Alternatively, $G_Z$ may be measured using a method in accordance with an embodiment of the invention as described below.

Figure 12:
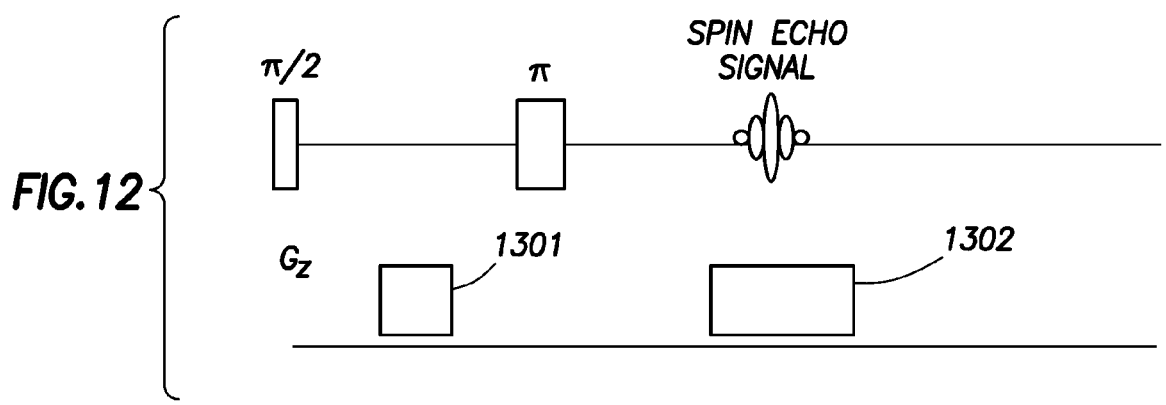
FIG. 12 shows a pulse sequence for generating a frequency-encoded spin-echo signal used in measuring an amplitude of a magnetic field gradient in accordance with an embodiment of the invention.

FIG. 12 shows a pulse sequence for measuring the amplitude of $G_Z$. A first magnetic field gradient 1301 is applied between the first and the second RF pulses. A second magnetic field gradient 1302 has a longer time duration than the first magnetic field gradient 1301, and extends over the time when the spin-echo signal is measured.

The NMR signal in the presence of the gradient is given by $$M(t)=\int \rho(z)\exp(-i\gamma G_Z zt)dt \qquad (13)$$

The Fourier transform of the signal M(t) gives the density distribution of spins:

$$\rho(Z)=\int M(t)\exp(i\gamma G_Z Zt)dz \qquad (14)$$

Figure 13:
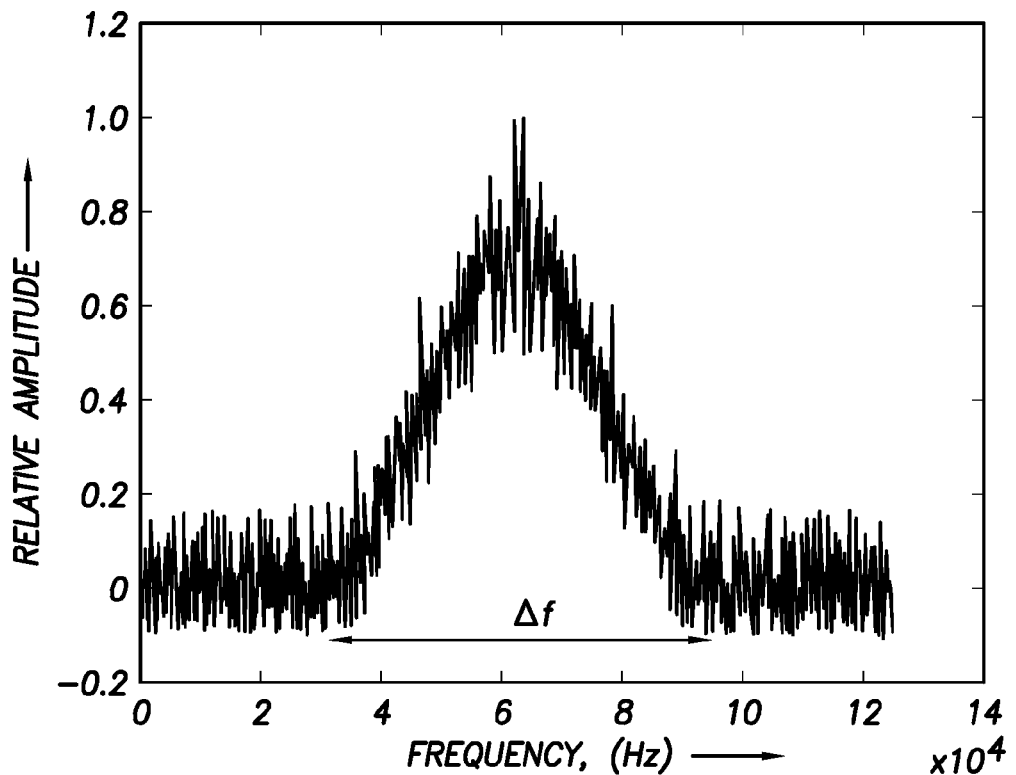
FIG. 13 shows a Fourier Transform of the frequency-encoded spin-echo signal.

The amplitude of the magnetic field gradient can be obtained from the Fourier transform of the spin-echo signal acquired in the presence of the gradient, called the frequency-encoded spin-echo signal. The Fourier-transformed NMR signal is shown in FIG. 13, The frequency spread ($\Delta f$) of the Fourier-transformed data depends on the amplitude of the gradient:

$$\Delta f=(\gamma/2\pi)dG_Z \qquad ,(15)$$

where $\gamma$ is the gyromagnetic ratio of protons, d is the length of the RF coil, and $G_Z$ amplitude of the field gradient applied along the RF coil.

Figure 4:
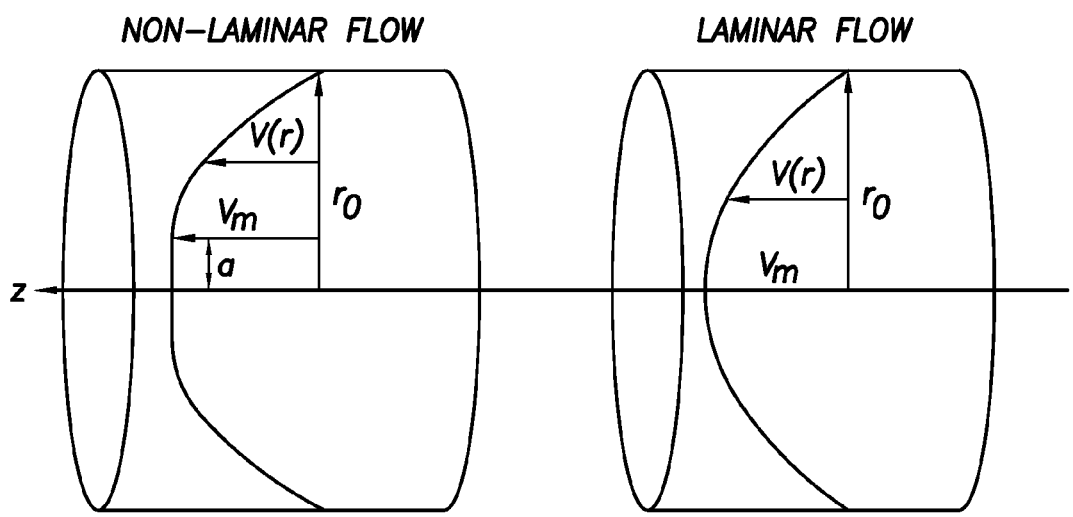
FIG. 4 illustrates a laminar flow and a non-laminar flow, respectively.
Figure 5:
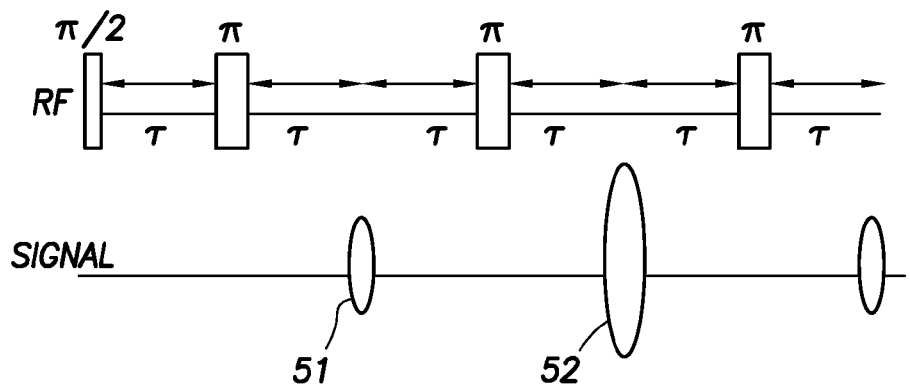
FIG. 5 shows a pulse sequence and corresponding spin-echo signal amplitudes for a flow velocity measurement in the prior art.
Figure 14:
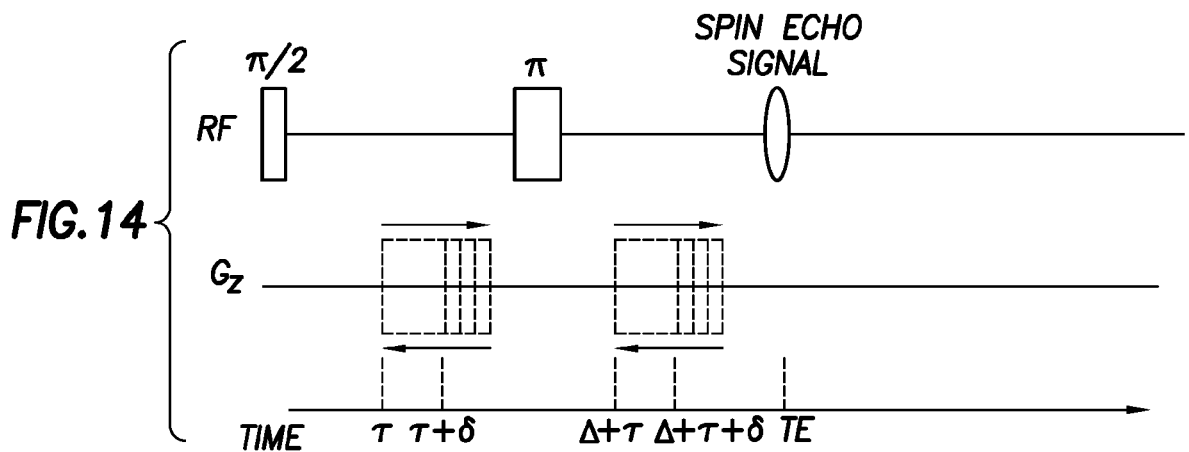
FIG. 14 shows a pulse sequence used in obtaining a velocity profile by varying a time duration of the magnetic field gradient.

The flow velocity of a fluid in a flowline is not homogeneous. As already shown in FIG. 4, depending on whether the flow is laminar flow or non-laminar flow, the flow velocity may be a 2-D function v(x, y). Further, in some flowlines the velocity Field is a 3-D function v(x, y, z). i.e., when the velocity varies along the flowline direction z. The velocity field profile of the flowing fluid in the flowline can be obtained from NMR imaging techniques. A pulse sequence for obtaining a velocity distribution, $\rho(v)$, is shown in FIG. 14. The pulse sequence includes a spin-echo sequence (90° and 180° RF pulses) and two gradient pulses of the same amplitude and the same time duration applied along the direction of the flowline before and after the 180° RF pulse, respectively. The sequence is repeated for different values of the gradient pulse time durations. The NMR signal, $M(\delta)$, is given by $$M(\delta)=\int \rho(v)\exp(-i\gamma G_Z v\Delta\delta)dv. \qquad (16)$$

The Fourier transform of the NMR signal $M(\delta)$ gives the velocity distribution $$\rho(v)=\int M(\delta)\exp(i\gamma G_Z v\Delta\delta)d\delta. \qquad (17)$$

Figure 15:
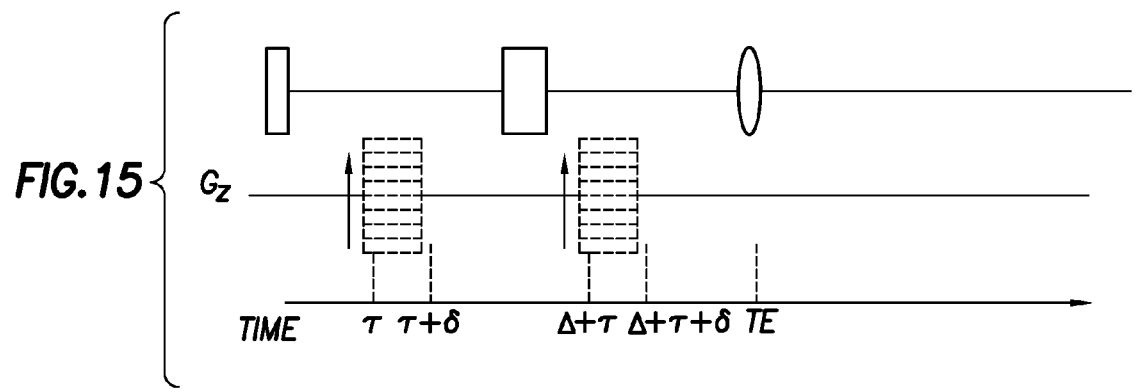
FIG. 15 shows a pulse sequence used in obtaining a velocity profile by varying an amplitude of the magnetic field gradient.

The velocity distribution can also be obtained by varying the amplitude of the magnetic field gradient pulses. A pulse sequence is shown in FIG. 15. The NMR signal is detected as a function of the gradient amplitude $$M(G_Z)=\int \rho(v)\exp(-i\gamma G_Z v\Delta\delta)dv. \qquad (18)$$

The Fourier transform of the signal gives the velocity distribution $$\rho(v)=\int M(G_Z)\exp(i\gamma G_Z v\Delta\delta)dG_Z \qquad .(19)$$

Figure 16:
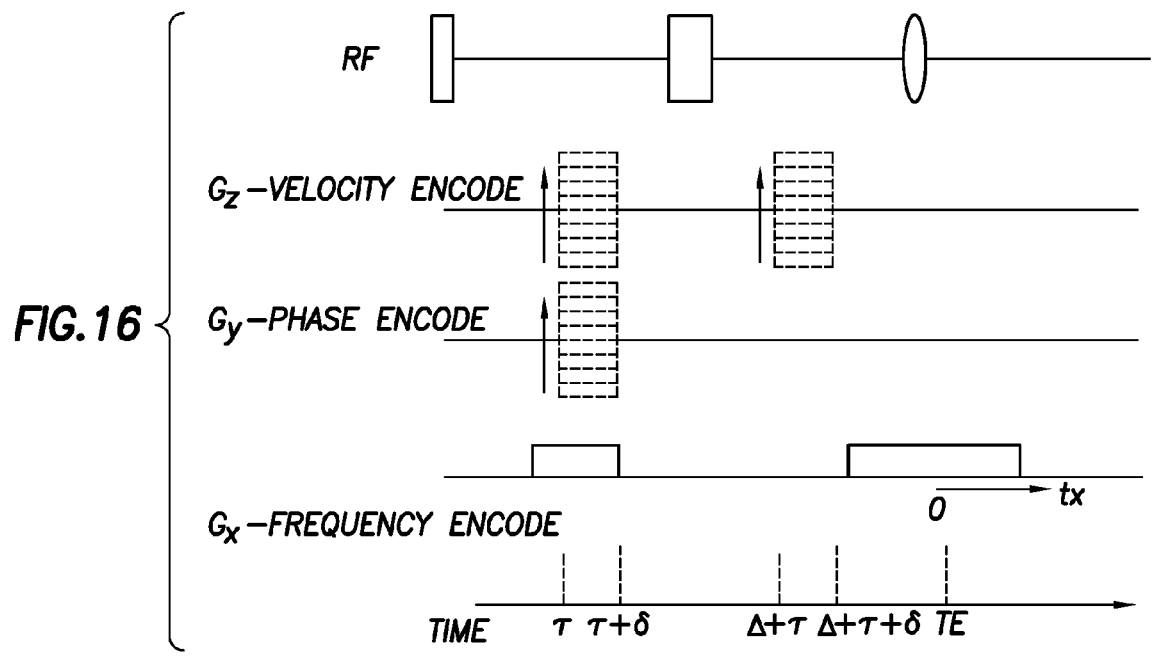
FIG. 16 shows a pulse sequence for velocity field imaging, including a velocity-encoded pulse, a phase-encoded pulse, and a frequency-encoded pulse.

The velocity distribution $\rho(v)$, in conjunction with flow models described by Eqs. (4a)-(5b), may be sufficient for deriving a 2-D or 3-D velocity image. Alternatively, 2-D or 3-D velocity image can be obtained using a pulse sequence in accordance with an embodiment of the invention, as shown in FIG. 16. The pulse sequence includes varying amplitude magnetic field gradient pulses along the flowline direction ($G_Z$), referred to as velocity-encoded pulses. It further includes a magnetic field gradient pulse in the Y direction ($G_Y$), also having varying amplitude, and referred to as a phase-encoded pulse, and frequency-encoded pulses in the X direction ($G_X$) that include a pulse at the time of the spin-echo signal (TE). Those of ordinary skill in the art will recognize that other combinations of pulse sequences known in the field of NMR imaging may be used to obtain a velocity image.

The NMR signal is given by $$S(k_x,k_y,k_v)=\int \rho(x,y)p(x,y,v)\exp(-ik_x\cdot x)\exp(-ik_y\cdot y)$$
$$\exp(-ik_v v)dx\,dy\,dv, \qquad (20)$$

where $\rho(x, y)$ is the spin density in the X-Y plane, $\rho(x, y, v)$ is the velocity distribution at each (x, y) location in a cross-section of the flow, v is the flow velocity, $k_x=\gamma G_x l_x$, $k_y=\gamma G_y \delta$, $k_v=\gamma G_Z\Delta\delta$, $\delta$ is the duration of the velocity-encoded and phase-encoded gradient pulses, and $\Delta$ is the time delay between two velocity-encoded gradient pulses.

Figure 17:
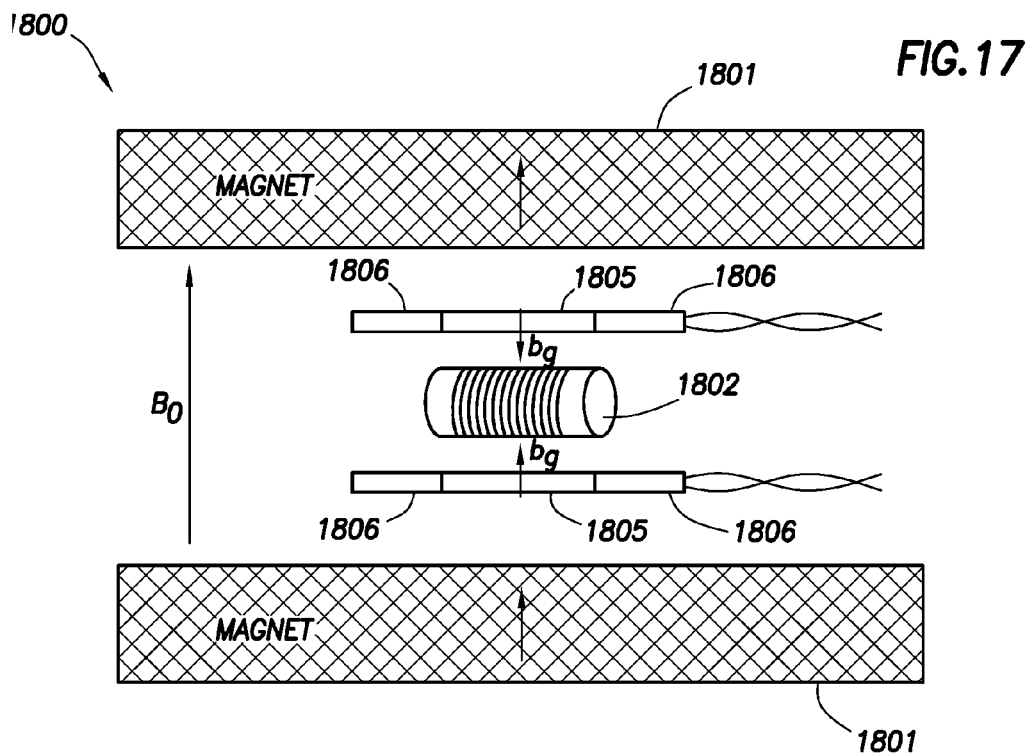
FIG. 17 shows an NMR sensor for imaging a velocity profile in accordance with an embodiment of die invention.

An NMR sensor in accordance with an embodiment of the invention is illustrated in FIG. 17 for velocity imaging utilizing Eq. (20). The NMR sensor 1800 includes a magnet 1801 for generating a substantially homogeneous magnetic field in a portion of the flowline 1802. Although in the exemplary configuration in FIG. 17, the magnet 1801 generates the homogeneous magnetic field $B_o$ perpendicular to the flowline direction, those of ordinary skill in the art will recognize that other directions of the homogeneous field can be used, so long as the homogeneous field defines a Larmor frequency for the system.

The NMR sensor 1800 also includes two sets of coils: 1805 for generating a magnetic field gradient substantially perpendicular to the flowline; and 1806 for generating a magnetic field gradient substantially along the flowline direction. Those of ordinary skill in the art will recognize that other means for generating a required magnetic field gradient may be used, e.g., coils or magnets having other configurations, so long as a magnetic field gradient can cause a measurable phase shift of the NMR signal. Note that a magnetic field gradient does not have to be along the flowline direction to cause a measurable phase shift. Different sets of coils can be used to generate pulsed field gradients in other directions to obtain (low parameter distributions in different directions.

Figure 18:
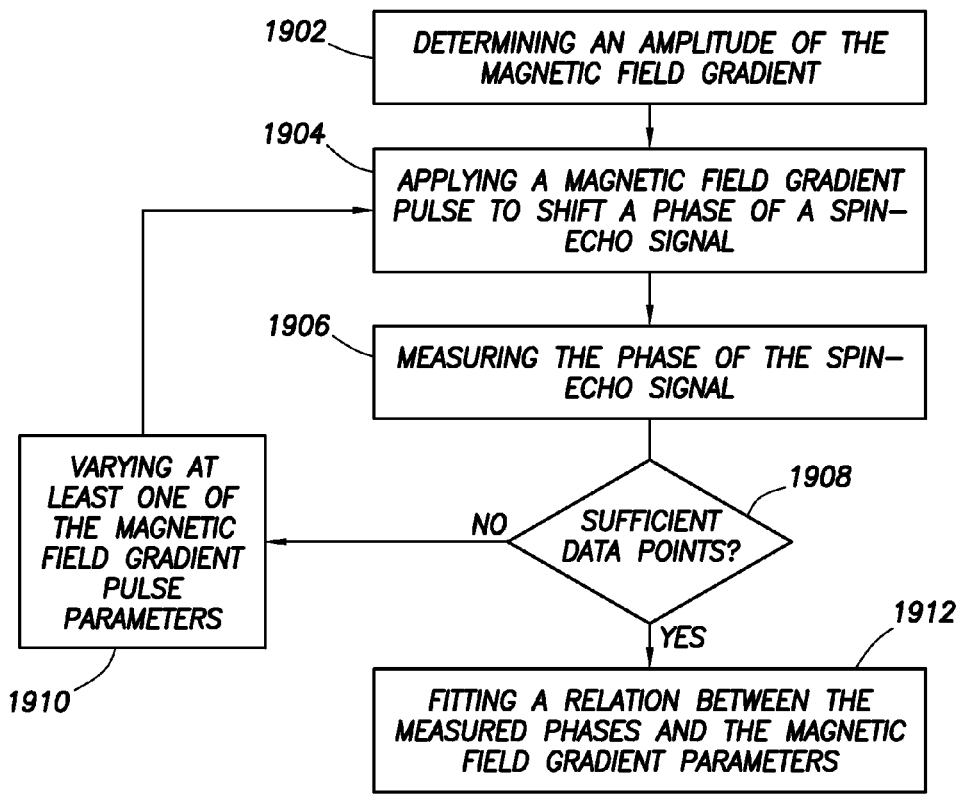
FIG. 18 is a flowchart showing a method of measuring a flow velocity in accordance with an embodiment of the invention It is to be understood that the drawings are to be used for the purpose of illustration only, and not as a definition of the metes and bounds of the invention, the scope of which is to be determined only by the scope of the appended claims.

A method of obtaining a flow velocity in accordance with an embodiment of the invention is summarized in the flowchart of FIG. 18. In step 1902, an amplitude of the magnetic field gradient is determined. A magnetic field gradient; pulse with a known amplitude is applied to cause a phase shift of an NMR spin-echo signal in step 1904. The phase of the spin-echo signal is measured in step 1906, If there are not enough data as determined in step 1908, one or more of the magnetic field gradient parameters are varied in step 1910, and the steps 1904 and 1906 are repeated until a sufficient number of data points are obtained. In step 1912, the data points are plotted, and a relation between the measured phase and the magnetic field gradient parameters is fitted to derive die flow velocity.

By measuring NMR signal phase instead of amplitude, the flow velocity can be derived without prior knowledge of the NMR relaxation times.

While the invention has been described with respect to a limited number of embodiments, those skilled in the art, having benefit of this disclosure, will appreciate that other embodiments can be envisioned that do not depart from the scope of the invention as disclosed herein. Accordingly, the scope of the invention shall be limited only by the attached claims.

What is claimed is:

1. A method to determine a velocity distribution of a fluid flowing in a flowline using a nuclear magnetic resonance (NMR) tool disposed in a wellbore, comprising:
    applying a radio frequency pulse sequence;
    applying a magnetic field gradient pulse sequence, wherein each magnetic field gradient pulse has parameters including a gradient magnetic field and a gradient pulse duration;
    measuring a NMR signal;
    determining a phase characteristic of the NMR signal;
    determining the velocity distribution of the fluid using the determined phase characteristic, the magnetic field gradient pulse parameters, and a time delay between gradient pulses; and
    outputting the velocity distribution of the fluid.

2. The method of claim 1, wherein the gradient magnetic field of each gradient pulse has a non-zero component along the direction of fluid flow.

3. The method of claim 1, further comprising repeating, for a desired number of times, the applying the radio frequency and gradient pulse sequences using different values of the gradient parameters, and the measuring NMR signals.

4. The method of claim 1, further comprising determining the gradient magnetic field magnitude.

5. The method of claim 1, wherein the velocity distribution is one-, two-, or three-dimensional.

6. The method of claim 5, wherein the velocity distribution yields the average velocity of the fluid.

7. The method of claim 1, wherein the measuring the NMR signal comprises measuring one or more spin-echo signals.

8. The method of claim 1, wherein the measuring the NMR signal includes measuring the NMR signal when the velocity of the fluid is zero.

9. A method to determine a velocity image of a fluid flowing in a flowline using a nuclear magnetic resonance tool disposed in a wellbore, comprising:
    applying a radio frequency pulse sequence;
    applying a magnetic field gradient pulse sequence, wherein each magnetic field gradient pulse has parameters including a gradient magnetic field and a gradient pulse duration;
    measuring a NMR signal;
    repeating, for a desired number of times, the applying the radio frequency and gradient pulse sequences using different values of the gradient parameters, and the measuring NMR signals;
    determining a phase characteristic from the NMR signals;
    determining the velocity image of the fluid using the determined phase characteristic, the magnetic field gradient pulse parameters, and a time delay between gradient pulses; and
    outputting the velocity image of the fluid.

10. The method of claim 9, wherein the applying the radio frequency and magnetic field gradient pulse sequences includes applying a gradient pulse in each of three orthogonal directions, wherein one of the three orthogonal directions is along the direction of fluid flow.

11. The method of claim 9, further comprising determining the gradient magnetic field magnitude.

12. The method of claim 9, wherein one or more velocity images may be used to determine a velocity distribution of the flowing fluid.

13. A downhole nuclear magnetic resonance apparatus to determine a velocity distribution of a fluid flowing in a flowline disposed in a downhole environment, comprising:
    a magnet configured to generate a substantially homogeneous magnetic field in a region of investigation;
    an antenna configured to receive an electromagnetic signal from the region of investigation;
    one or more coils configured to generate a magnetic field gradient pulse sequence, wherein each magnetic field gradient pulse has parameters including a magnetic field gradient and a gradient pulse duration;
    an electronics module to determine a NMR signal from the electromagnetic signal received by the antenna; and
    a processor to determine a phase characteristic from the NMR signal and the velocity distribution of the fluid using the determined phase characteristic, the magnetic field gradient pulse parameters, and a time delay between gradient pulses.

14. The apparatus of claim 13, wherein the one or more coils generate a magnetic field gradient having components in three orthogonal directions.

15. The apparatus of claim 13, wherein the region of investigation can be in a flowline, in a formation surrounding the wellbore, or in the wellbore.

16. A downhole system to determine a flow property of a formation fluid flowing in a flowline, comprising:
    a formation fluid testing tool; and
    a nuclear magnetic resonance tool comprising:
        a magnet configured to generate a substantially homogeneous magnetic field in a region of investigation;
        an antenna configured to receive an electromagnetic signal from the region of investigation;
        one or more coils configured to generate a magnetic field gradient pulse sequence, wherein each magnetic field gradient pulse has parameters including a magnetic field gradient and a gradient pulse duration;

an electronics module to determine a NMR signal from the electromagnetic signal received by the antenna; and a processor to determine a phase characteristic from the NMR signal and the velocity distribution of the fluid using the determined phase characteristic, the magnetic field gradient pulse parameters, and a time delay between gradient pulses.

17. The system of claim 16, wherein the formation fluid testing tool comprises a probe module and a pumping module.

18. The system of claim 16, wherein the nuclear magnetic resonance tool is incorporated into the formation fluid testing tool.

* * * * *